(12) United States Patent
Patel et al.

(10) Patent No.: US 10,405,862 B2
(45) Date of Patent: Sep. 10, 2019

(54) LAPAROSCOPIC CLIP APPLIER

(71) Applicant: Applied Medical Resources Corporation, Rancho Santa Margarita, CA (US)

(72) Inventors: Atal C. Patel, Mission Viejo, CA (US); Michael Whitlock, Irvine, CA (US); Patrick Elliott, Rancho Santa Margarita, CA (US); Andrew J. McCarthy, Trabuco Canyon, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 313 days.

(21) Appl. No.: 15/493,682

(22) Filed: Apr. 21, 2017

(65) Prior Publication Data

US 2017/0303921 A1    Oct. 26, 2017

Related U.S. Application Data

(60) Provisional application No. 62/325,541, filed on Apr. 21, 2016.

(51) Int. Cl.
*A61B 17/10* (2006.01)
*A61B 17/00* (2006.01)
(Continued)

(52) U.S. Cl.
CPC ........ *A61B 17/10* (2013.01); *A61B 17/00234* (2013.01); *A61B 17/1285* (2013.01);
(Continued)

(58) Field of Classification Search
CPC ... A61B 17/10; A61B 17/128; A61B 17/1285; A61B 17/068; A61B 17/0682;
(Continued)

(56) References Cited

U.S. PATENT DOCUMENTS

| 5,030,226 A | 7/1991 | Green et al. |
| 5,171,249 A | 12/1992 | Stefanchik et al. |

(Continued)

FOREIGN PATENT DOCUMENTS

| CN | 201683954 U | 12/2010 |
| EP | 2 361 562 A1 | 8/2011 |
| WO | WO 2015/071614 A1 | 5/2015 |

OTHER PUBLICATIONS

European Patent Office, The International Search Report and Written Opinion for International Application No. PCT/US2017/028813, entitled "Laparoscopic Clip Applier," dated Jul. 18, 2017, 27 pgs.

*Primary Examiner* — Melanie R Tyson
(74) *Attorney, Agent, or Firm* — John F. Heal

(57) ABSTRACT

A laparoscopic clip applier can have a geared clip feed mechanism and a direct jaw clamping mechanism to provide smooth operation over a clip application stroke of a movable handle. The geared clip feed mechanism can include an idler gear and two drive gear racks to advance a feed slider feeding a clip to a jaw assembly. The two drive gear racks can be positioned to provide different gearing during clip feed and firing portions of the clip application stroke, allowing efficient packaging of the clip feed mechanism. A spring can rapidly withdraw the feed slider once the clip has been fed and before clamping begins. The movable handle can have a direct connection to a clamping slider to enhance user feedback during clamping of the clip. After clamping the clip, the movable handle can also assist in returning the clamping slider to an initial position for firing another clip.

23 Claims, 18 Drawing Sheets

(51) Int. Cl.
 *A61B 17/128* (2006.01)
 *A61B 17/29* (2006.01)

(52) U.S. Cl.
 CPC ............... *A61B 2017/0046* (2013.01); *A61B 2017/00407* (2013.01); *A61B 2017/2923* (2013.01)

(58) Field of Classification Search
 CPC .. A61B 2017/0488; A61B 2017/00367; A61B 2017/00407; A61B 2017/0046; A61B 2017/2923
 See application file for complete search history.

(56) References Cited

U.S. PATENT DOCUMENTS

| | | |
|---|---|---|
| 5,514,149 A | 5/1996 | Green et al. |
| 5,582,615 A | 12/1996 | Foshee et al. |
| 5,607,436 A | 3/1997 | Pratt et al. |
| 5,700,271 A | 12/1997 | Whitfield et al. |
| 5,782,844 A | 7/1998 | Yoon et al. |
| 5,830,221 A | 11/1998 | Stein et al. |
| 6,099,537 A | 8/2000 | Sugai et al. |
| 6,425,900 B1 | 7/2002 | Knodel et al. |
| 6,551,333 B2 | 4/2003 | Kuhns et al. |
| 6,572,626 B1 | 6/2003 | Knodel et al. |
| 7,261,724 B2 | 8/2007 | Molitor et al. |
| 7,288,098 B2 | 10/2007 | Huitema et al. |
| 7,297,149 B2 | 11/2007 | Vitali et al. |
| 7,419,495 B2 | 9/2008 | Menn et al. |
| 7,637,917 B2 | 12/2009 | Whitfield et al. |
| 7,670,362 B2 | 3/2010 | Zergiebel |
| 7,686,820 B2 | 3/2010 | Huitema et al. |
| 7,717,926 B2 | 5/2010 | Whitfield et al. |
| 7,731,724 B2 | 6/2010 | Huitema et al. |
| 7,740,641 B2 | 6/2010 | Huitema |
| 7,833,234 B2 | 11/2010 | Bailly et al. |
| 7,862,573 B2 | 1/2011 | Darois et al. |
| 7,875,040 B2 | 1/2011 | Bright |
| 7,905,890 B2 | 3/2011 | Whitfield et al. |
| 8,021,375 B2 | 9/2011 | Aldrich et al. |
| 8,038,686 B2 | 10/2011 | Huitema et al. |
| 8,075,571 B2 | 12/2011 | Vitali et al. |
| 8,080,004 B2 | 12/2011 | Downey et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,679 B2 | 9/2012 | Nguyen |
| 8,267,945 B2 | 9/2012 | Nguyen et al. |
| 8,282,655 B2 | 10/2012 | Whitfield et al. |
| 8,328,822 B2 | 12/2012 | Huitema et al. |
| 8,357,171 B2 | 1/2013 | Whitfield et al. |
| 8,382,773 B2 | 2/2013 | Whitfield et al. |
| 8,409,223 B2 | 4/2013 | Sorrentino et al. |
| 8,419,752 B2 | 4/2013 | Sorrentino et al. |
| 8,465,502 B2 | 6/2013 | Zergiebel |
| 8,491,608 B2 | 7/2013 | Sorrentino et al. |
| 8,496,673 B2 | 7/2013 | Nguyen et al. |
| 8,518,055 B1 | 8/2013 | Cardinale et al. |
| 8,523,882 B2 | 9/2013 | Huitema et al. |
| 8,579,920 B2 | 11/2013 | Nering et al. |
| 8,728,098 B2 | 5/2014 | Daniel et al. |
| 8,728,099 B2 | 5/2014 | Cohn et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,915,930 B2 | 12/2014 | Huitema et al. |
| 8,920,439 B2 | 12/2014 | Cardinale et al. |
| 9,017,345 B2 | 4/2015 | Taylor et al. |
| 9,089,334 B2 | 7/2015 | Sorrentino et al. |
| 2004/0097972 A1 | 5/2004 | Shipp et al. |
| 2006/0079913 A1 | 4/2006 | Whitfield et al. |
| 2014/0303650 A1 | 10/2014 | Vitali et al. |
| 2014/0330291 A1 | 11/2014 | Whitfield et al. |
| 2014/0343578 A1 | 11/2014 | Huitema |

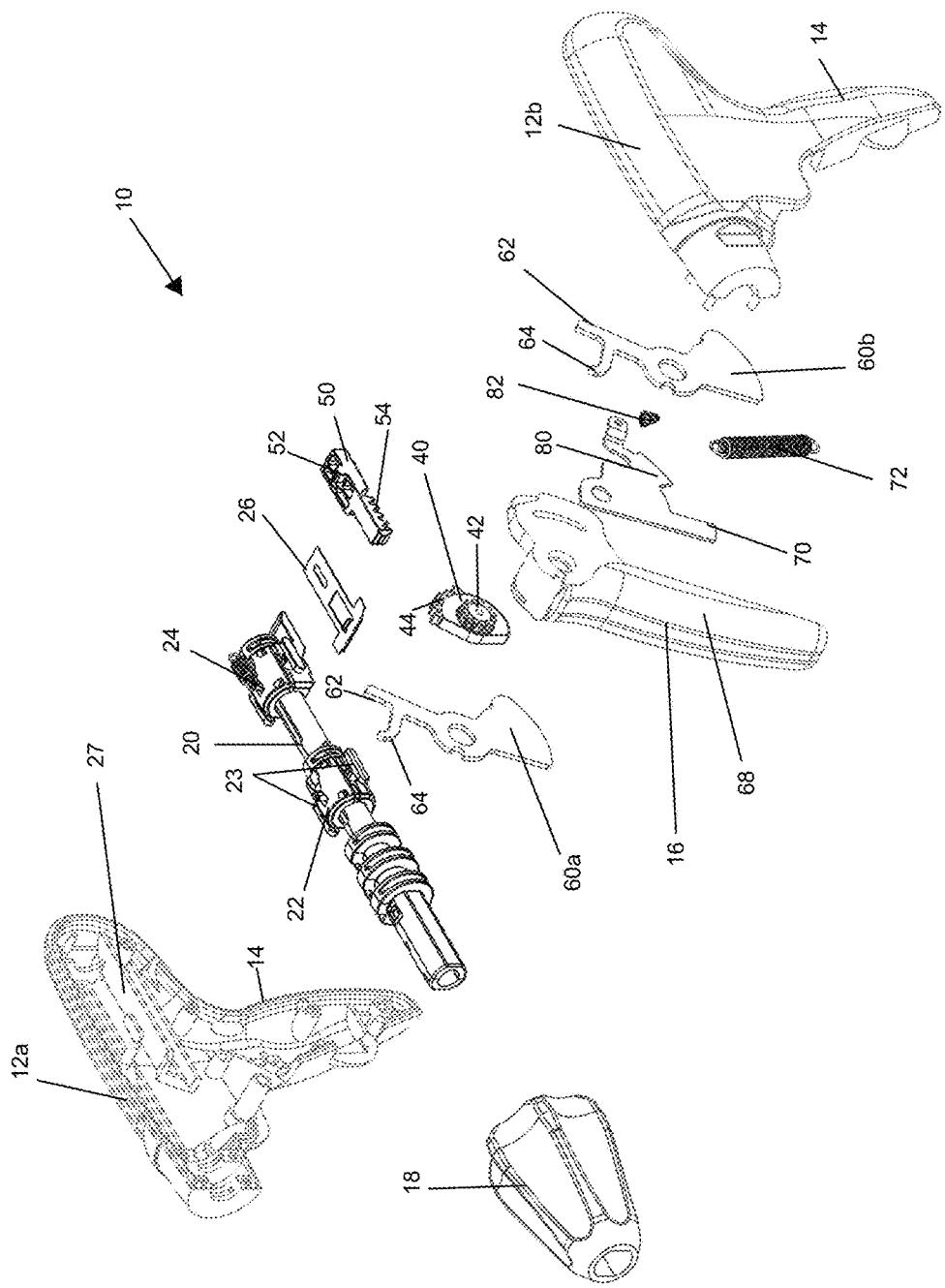

LAPAROSCOPIC CLIP APPLIER

CROSS REFERENCE TO RELATED APPLICATION

This application claims the benefit of U.S. Provisional Patent Application Ser. No. 62/325,541, entitled "LAPAROSCOPIC CLIP APPLIER," filed Apr. 21, 2016, currently pending. The above-referenced application is incorporated by reference herein in its entirety.

BACKGROUND OF THE INVENTION

Field of the Invention

The present application relates to surgical instruments and more particularly to surgical clip appliers for use in minimally invasive surgical procedures.

Description of the Related Art

Endoscopic surgery can frequently require the application of hemostatic clips or the use of other instruments which can ligate, grab, or grip for a variety of purposes. Several significant characteristics of such instruments are simplicity in construction, reliability in operation, as well as low cost. Components that come into contact with internal organs in the body must also be effectively sterilized. Alternatively, the construction can desirably be sufficiently economical to allow disposability of contaminated components. The layout of the instrument should desirably give the surgeon good feedback during the procedure to allow as much control as possible while using the instrument.

Previous hemostatic clip appliers have had various shortcomings. For example, certain clip appliers have been overly complex, adding to manufacturing costs and time. Previous clip appliers have also provided inadequate user feedback, with inconsistent grip force profiles or relatively high grip force requirements during loading and closure of a clip.

SUMMARY OF THE INVENTION

In certain embodiments, a laparoscopic surgical clip applier is provided herein. The surgical clip applier comprises a jaw assembly, a shaft assembly, and a handle assembly. The jaw assembly comprises a pair of opposed jaws configured to receive and clamp a surgical clip. The shaft assembly extends from a proximal end to a distal end. The jaw assembly is positioned at the distal end of the shaft assembly. The shaft assembly comprises a clamping slider and a feed slider disposed at the proximal end thereof. The handle assembly is disposed at the proximal end of the shaft assembly. The handle assembly comprises: a stationary handle, a movable handle, a clamping actuator, and a feed mechanism. The movable handle is pivotably coupled to the stationary handle. The clamping actuator is coupled to the movable handle. The clamping actuator comprises a clamping fork and a return fork. The clamping fork extends from the clamping actuator and is configured to distally advance the clamping slider. The return fork extends from the clamping actuator and is configured to proximally retract the clamping slider. The feed mechanism comprises an idler gear and a slider. The idler gear is rotatably driven by the movable handle. The idler gear comprises a first plurality of drive teeth and a second plurality of drive teeth. The slider is longitudinally movable within the handle assembly. The slider comprises a first gear rack engageable with the first plurality of drive teeth and a second gear rack engageable with the second plurality of drive teeth. The slider is engageable with the feed slider.

In certain embodiments, a laparoscopic surgical clip applier is provided herein. The laparoscopic clip applier comprises a jaw assembly, a shaft assembly, and a handle assembly. The jaw assembly comprises a pair of opposed jaws configured to receive and clamp a surgical clip. The shaft assembly extends from a proximal end to a distal end. The jaw assembly is positioned at the distal end of the shaft assembly. The shaft assembly comprises a plurality of surgical clips disposed within the shaft assembly. The handle assembly is disposed at the proximal end of the shaft assembly. The handle assembly comprises a stationary handle, a movable handle, a feed mechanism, and a clamping mechanism. The movable handle is pivotably coupled to the stationary handle. The feed mechanism comprises a gear train coupled to the movable handle and coupled to the shaft assembly to feed a distal surgical clip of the plurality of surgical clips into the jaw assembly. The clamping mechanism is coupled to the jaw assembly to clamp the pair of opposed jaws of the jaw assembly. The movable handle is movable from a spaced apart configuration relative to the stationary handle to an approximated configuration relative to the stationary handle. The movable handle is movable over a first distance from the spaced apart configuration to actuate the feed mechanism and movable over a second distance from the first distance to the approximated configuration to actuate the clamping mechanism.

In certain embodiments, a laparoscopic surgical clip applier is provided herein. The laparoscopic clip applier comprises a jaw assembly, a shaft assembly, and a handle assembly. The jaw assembly comprises a pair of opposed jaws configured to receive and clamp a surgical clip. The shaft assembly extends from a proximal end to a distal end. The jaw assembly is positioned at the distal end of the shaft assembly. The shaft assembly comprises a first slider and a second slider at the proximal end. The handle assembly comprises a stationary handle, a movable handle, a first actuation mechanism, and a second actuation mechanism. The movable handle is pivotably coupled to the stationary handle. The first actuation mechanism is coupled to the movable handle and to the first slider. The second actuation mechanism comprises a drive gear and a longitudinal slider. The drive gear is rotatably driven by pivotal movement of the movable handle. The drive gear has a first plurality of teeth and a second plurality of teeth. The longitudinal slider has a first rack engageable with the first plurality of teeth and a second rack engageable with the second plurality of teeth. The longitudinal slider is engageable with the second slider of the shaft assembly.

BRIEF DESCRIPTION OF THE DRAWINGS

FIG. 4 is an exploded perspective view of the handle assembly of FIG. 1;

DETAILED DESCRIPTION OF THE INVENTION

Figure 1:
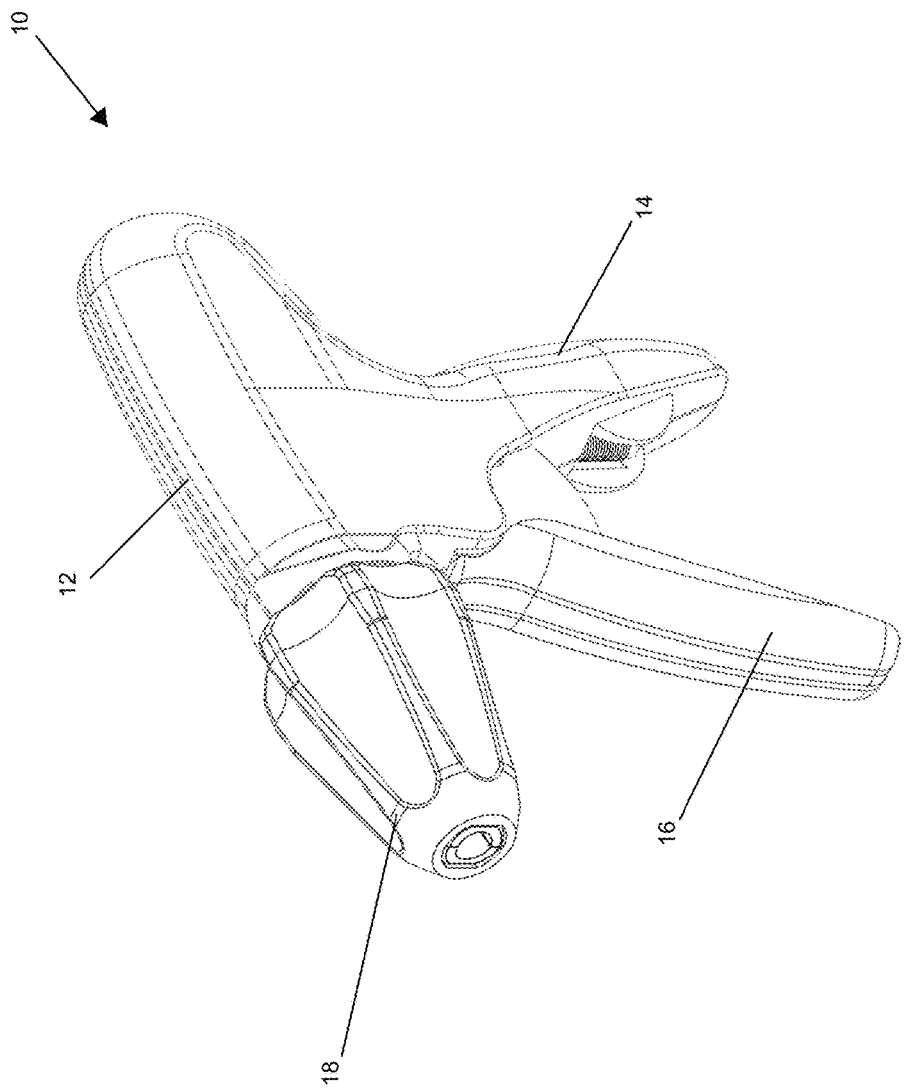
FIG. 1 is a perspective view of view of an embodiment of handle assembly for a laparoscopic clip applier.
Figure 2:
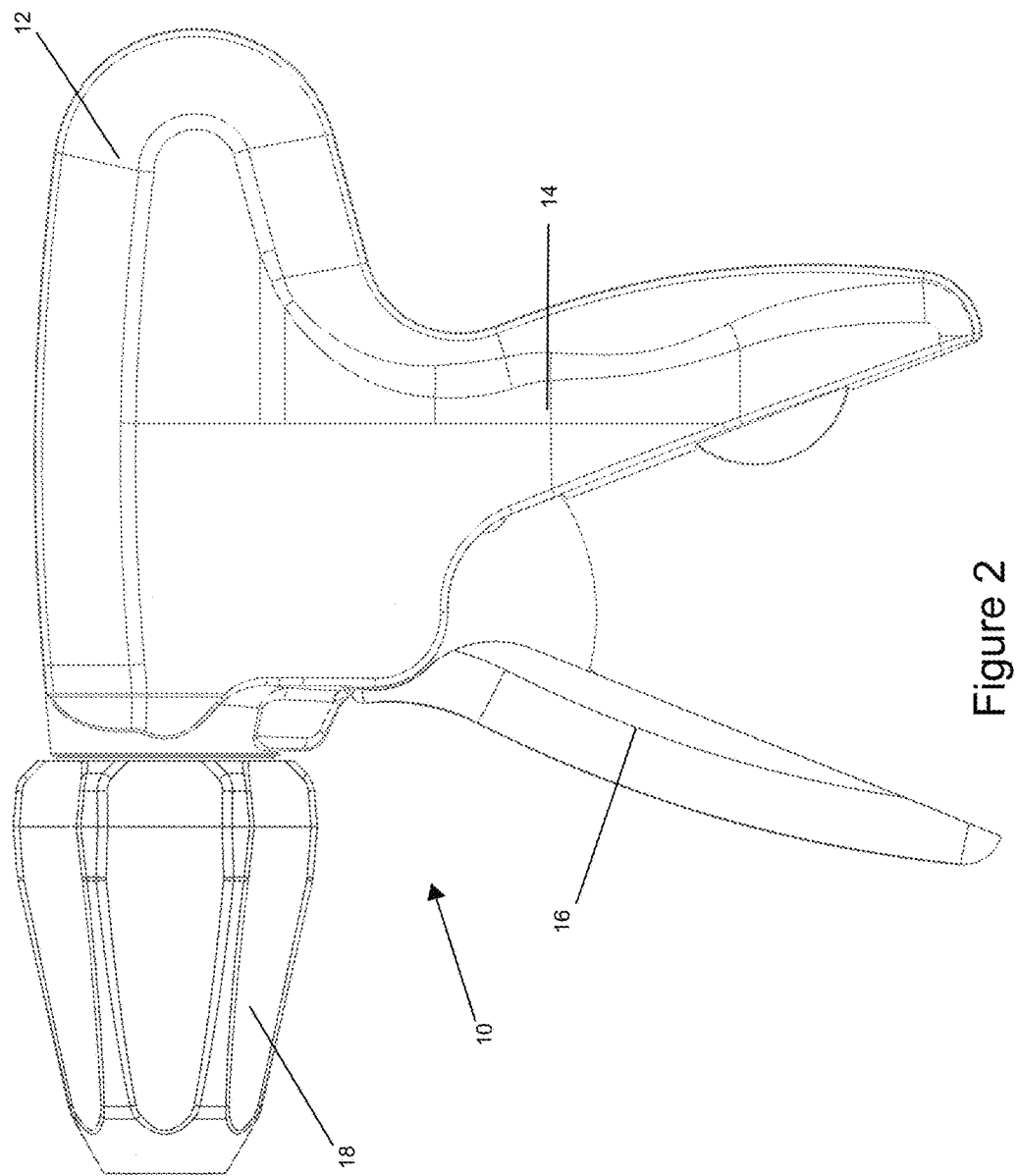
FIG. 2 is a side view of the handle assembly of FIG. 1.

With reference to FIGS. 1 and 2, an embodiment of a handle assembly 10 for a laparoscopic clip applier is illustrated. The handle assembly 10 can comprise a handle body 12 extending from a proximal end to a distal end and defining a longitudinal axis of the handle assembly. The handle body 12 has a stationary handle 14 and a movable handle 16 or trigger pivotably coupled to the stationary handle 14. The movable handle 16 can be pivoted from a spaced apart or open configuration relative to the stationary handle 14 to an approximated or closed configuration. The handle assembly 10 further comprises a laparoscopic shaft interface at the distal end of the handle body 12. The laparoscopic shaft interface can have a rotatable collar 18 that is rotatable about the longitudinal axis to rotate a laparoscopic shaft and jaw assembly coupled to the laparoscopic shaft interface.

In the illustrated embodiment, the handle assembly 10 comprises a pistol-grip style handle with a stationary handle 14 and a movable handle 16 coupled thereto. But, it is contemplated that in other embodiments, other handle styles can include some or all of the features further described with respect to the illustrated pistol-grip handle. For example, the handle assembly can comprise a scissor-type handle, a generally in-line handle, or another handle style.

Figure 3A:
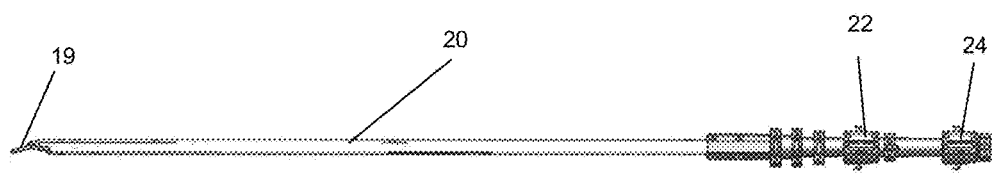
FIG. 3A is a side view of an embodiment of shaft assembly and a jaw assembly for an embodiment of laparoscopic clip applier.
Figure 3B:
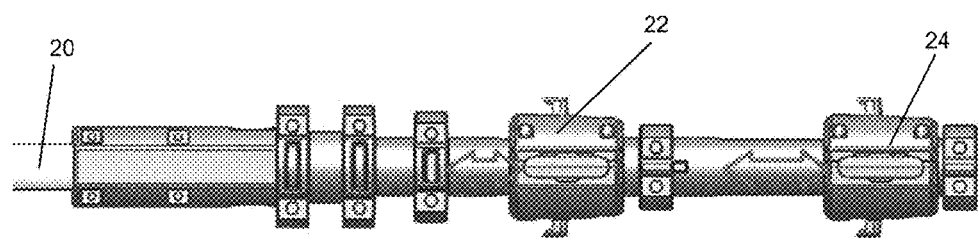
FIG. 3B is a side detail view of the proximal end of the shaft assembly of FIG. 3A.

With reference to FIGS. 3A and 3B, an embodiment of laparoscopic shaft assembly 20 and jaw assembly 19 that can be used with the handle assembly of FIG. 1 is illustrated. The shaft extends generally longitudinally from a proximal end to a distal end. A jaw assembly 19 comprising a pair of opposing jaws is disposed at the distal end. A central portion extends between the proximal end and the distal end. An actuation assembly is positioned at the proximal end. The jaw assembly is configured to receive a surgical clip when the jaws are in an open configuration with one jaw spaced apart from an opposing jaw. Once the jaw assembly has received the surgical clip, the jaws are clamped to a closed configuration in which the jaws are approximated to clamp the surgical clip. The jaw assembly 19 can then be returned to the open configuration to receive another clip.

With continued reference to FIGS. 3A and 3B, the central portion of the shaft assembly 20 comprises a generally tubular member extending from the proximal end to the distal end. The tubular member has a generally smooth outer surface to be positioned through a seal interface of a surgical access port such as a trocar cannula. A plurality of surgical clips can be positioned within the tubular member. Furthermore, the shaft assembly can comprise a mechanism for feeding the distal-most clip of the plurality of surgical clips to the jaw assembly and a mechanism for closing the jaws of the jaw assembly. The tubular member and jaw assembly can be sized for insertion through a surgical access port having a specific inner diameter. For example, the tubular member and jaw assembly can be sized for insertion through a 15 mm, 12 mm, 10 mm, 8 mm, or 5 mm trocar cannula or a surgical access port having another inner diameter.

With continued reference to FIGS. 3A and 3B, the proximal end of the shaft assembly 20 comprises the actuation assembly. When the shaft assembly is assembled with a surgical clip applier, the actuation assembly is positioned within the handle assembly. As illustrated, the actuation assembly comprises a first slider 22 positioned at the distal end of the actuation assembly. The actuation assembly can further comprise a second slider 24 positioned at the proximal end of the actuation assembly. The first and second sliders 22, 24 can each be longitudinally slid with respect to the shaft assembly. Sliding of the first and second sliders 22, 24 can actuate clip feed and closure mechanisms within the shaft assembly to sequentially feed a distal-most clip from the plurality of clips into the jaw assembly and clamp the clip. As further discussed with respect to the handle assembly, in the illustrated embodiment, the first slider 22 is coupled to the closure mechanism and the second slider 24 is coupled to the clip feed mechanism. In other embodiments, it is contemplated that the first slider 22 can be coupled to the feed mechanism and the second slider 24 can be coupled to the closure mechanism and that the handle assembly can be configured to operate the first and second sliders 22, 24 in an appropriate sequence to feed and clamp a surgical clip.

With reference to FIG. 3B, as illustrated, the second slider 24 is coupled to the feed mechanism within the shaft assembly. As the second sider 24 is advanced longitudinally distally by the handle assembly, a clip of the plurality of clips in the tubular member is loaded into the jaw assembly. The second slider 24 is then retracted proximally by the handle assembly leaving the clip positioned in the jaw assembly 19. Retracting the second slider 24 proximally can also retract the feed mechanism from the jaw assembly 19 such that the jaw assembly 19 is able to be closed without interference from the feed mechanism.

With reference to FIG. 3B, as illustrated, the first slider 22 is coupled to the closure mechanism within the shaft assembly. When the first slider 22 is advanced longitudinally distally by the handle assembly, the closure mechanism is operated to approximate the jaws of the jaw assembly and compress the surgical clip loaded between the jaws of the jaw assembly 19. When the first slider 22 is retracted proximally, the jaw assembly 19 returns to the open configuration.

With reference to FIG. 4, an exploded view of the handle assembly 10 of FIGS. 1 and 2 is illustrated. In the illustrated embodiment, the handle body comprises two housing halves 12a, 12b that can be joined such as with a snap-fit construction or fasteners to enclose the handle assembly. The actuation assembly of the shaft can extend longitudinally within the handle body. The stationary handle 14 can be formed integrally with the handle body. The movable handle 16 can be pivotally coupled to the housing halves 12a, 12b of the handle body at a pivot point.

With continued reference to FIG. 4, in the illustrated embodiment, the movable handle 16 comprises a layered construction. As illustrated, the movable handle 16 comprises a grip member 68, a first closure lever 60a, a second closure lever 60b, and a ratchet plate 70, all of which are layered together and rotatable about the pivot point. The grip member 68, first closure lever 60a, second closure lever 60b, and ratchet plate 70 are joined such that they rotate about the pivot point as a single unit. For example, in some embodiments, the individual layers of the movable handle can each include a keyed coupling to an adjacent layer. In other embodiments, the individual layers can be fastened to one another with fasteners, adhesives, welding or other fusing techniques. In still other embodiments, the movable handle can be integrally formed as a monolithic unit.

With continued reference to FIG. 4, in the illustrated embodiment, the handle assembly further comprises a feed mechanism having a gear train. In the illustrated embodiment, the gear train comprises an idler gear 40, a longitudinal slider 50, and a drive plate 26. The idler gear 40 is driven responsive to pivoting movement of the movable handle 16. The idler gear 40 is rotatably coupled to the handle body 12 and rotates about an axis that extends through an arcuate slot formed in the movable handle 16. The idler gear 40 can comprise a pinion gear portion 42 and at least one drive gear portion including a plurality of gear teeth 44. The pinion gear portion 42 is positioned to be driven by a plurality of drive gear teeth disposed on the movable handle 16.

With continued reference to FIG. 4, in the illustrated embodiment, the idler gear 40 is in geared engagement with the longitudinal slider 50. Thus, rotation of the idler gear 40 responsive to pivotal motion of the movable handle 16 rotates the at least one drive gear portion of the idler gear 40, which engages a corresponding at least one rack portion 54 of the longitudinal slider 50. The longitudinal slider 50 is positioned on a longitudinal shelf 27 within the handle body 12 adjacent the actuation assembly. Accordingly, pivotal movement of the movable handle 16 is transmitted through the gear train of the feed mechanism to result in longitudinal sliding of the longitudinal slider 50.

With continued reference to FIG. 4, the longitudinal slider 50 can include a protrusion 52 that is engageable with the drive plate 26. The drive plate 26 can be coupled to the second slider 24 such that with the longitudinal slider 50 engaged with the drive plate 26, longitudinal movement of the longitudinal slider 50 correspondingly moves the second slider 24 of the actuation assembly.

The first slider 22 of the actuation assembly is coupled to the movable handle 16 by a closure mechanism. In the illustrated embodiment, the closure mechanism comprises the first closure lever 60a and the second closure lever 60b coupled to the movable handle 16. The first closure lever 60a and second closure lever 60b are positioned laterally on opposite sides of the first slider 22. The first closure lever 60a and second closure lever 60b each comprise a forked end having a closure fork 62 and a retraction fork 64. The first slider 22 comprises laterally-extending protrusions such as lugs 23 that can be engaged by the forked ends of the first and second closure levers 60a, 60b to longitudinally advance or retract the first slider 22 responsive to pivotal movement of the movable handle 16.

With continued reference to FIG. 4, the handle assembly can further comprise a ratchet mechanism. The ratchet mechanism can be coupled to the movable handle 16 to prevent the movable handle from being released before a loaded clip has been clamped a predetermined amount. Advantageously, this ratchet mechanism can reduce the incidence of clip jams or unintended deployment of insufficiently clamped clips. In the illustrated embodiment, the ratchet mechanism comprises the ratchet plate 70 having a ratchet rack 80 formed thereon and a pawl 82 engageable with the ratchet rack 80. The pawl 82 is coupled to the handle body 12 and is positioned to engage with the ratchet rack 80 once the movable handle 16 has been pivoted an initial increment from an open configuration.

In operation in conjunction with a clip feeding and clamping cycle, once the pawl 82 engages the ratchet rack 80, the ratchet mechanism allows continued movement of the movable handle 16 towards the approximated configuration, but restricts movement of the movable handle 16 toward the open configuration. Once the movable handle 16 has been pivoted to feed a clip to the jaw assembly and clamp the clip a predetermined amount, the pawl 82 reaches an end of the ratchet rack 80 and disengages from the ratchet rack 80. With the pawl 82 disengaged from the ratchet rack 80, the movable handle 16 can be released to pivot towards the open configuration. The handle assembly can include a biasing member such as a tension spring 72 that biases the movable handle 16 towards the open configuration.

Figure 5:
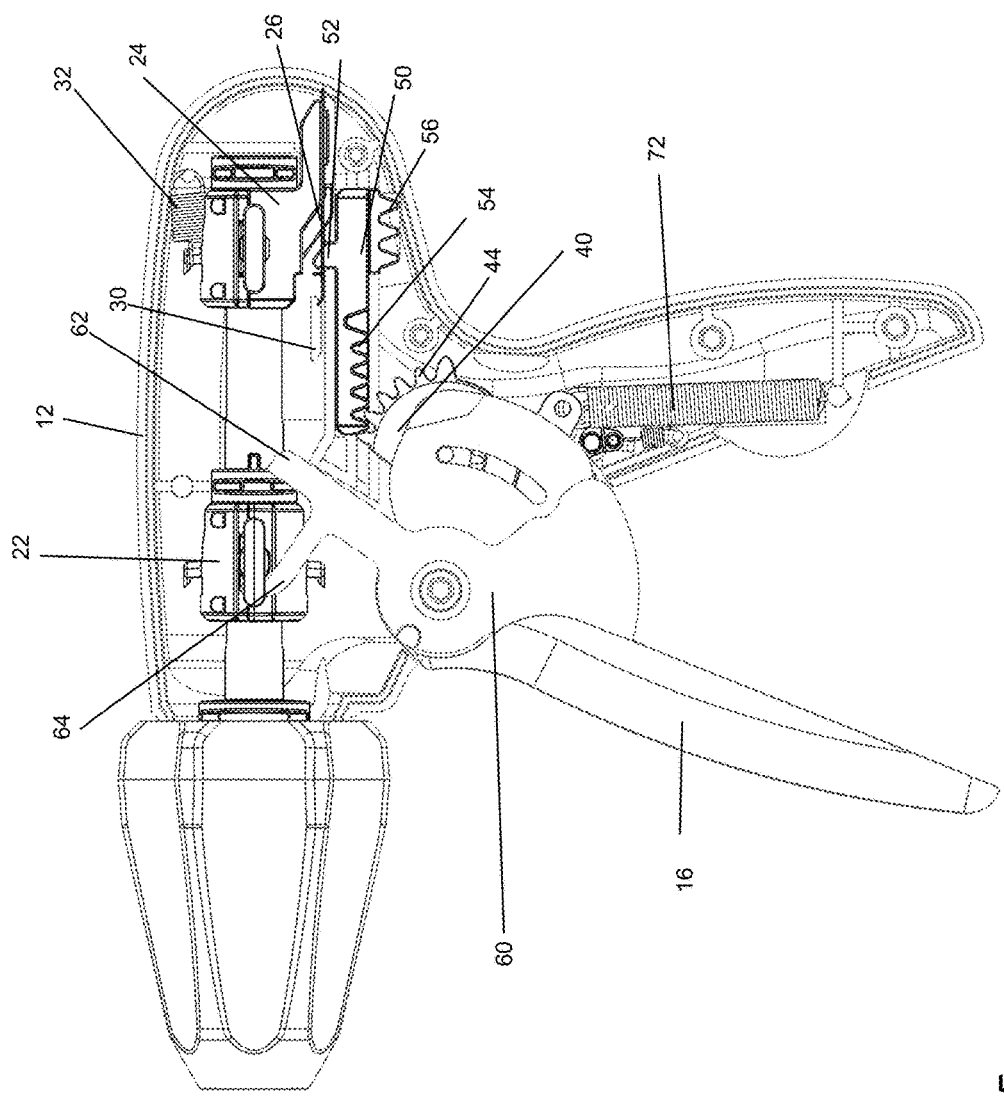
FIG. 5 is a cut-away side view of the handle assembly of FIG. 1 with handles in a spaced apart configuration.

With reference to FIGS. 5-12, a complete clip feed and closure cycle of the handle assembly is illustrated. With reference to FIG. 5, a partial cut away view of the handle assembly illustrates the handle assembly with the movable handle 16 in an initial, open configuration. With the handle in the open configuration, the first and second sliders 22, 24 of the actuation assembly are each in fully proximally retracted positions and no clip is present in the jaw assembly.

With the handle assembly in the open configuration, the closure fork 62 of the closure mechanism is disengaged from the first slider 22 of the actuation assembly. Rather, the retraction fork 64 of the closure mechanism can engage the first slider 22, with a fork gap between the retraction fork 64 and the closure fork 62 separating the closure fork 62 from the first slider 22. Accordingly, upon initial movement of the movable handle 16, the closure lever 60 is directly pivoted by the movable handle 16, but the closure mechanism does not engage the first slider 22.

With the handle assembly in the open configuration, the drive gear portion 44 of the idler gear 40 in the gear train of the feed mechanism is in meshed engagement with the corresponding drive rack portion 54 of the longitudinal slider 50. As illustrated, the longitudinal slider 50 is in a proximal position. Upon initial movement of the movable handle 16, the idler gear 40 will rotate and advance the longitudinal slider 50 distally. Additionally, with the longitudinal slider 50 in the proximal position, the protrusion 52 or fin of the longitudinal slider 50 can engage the drive plate 26. Thus, when the longitudinal slider 50 is advanced distally, the drive plate 26 and second slider 24 are correspondingly advanced distally. The longitudinal slider 50, drive plate 26, and second slider 24 can be biased to the proximal position by a biasing member such as a tension spring 32 coupled to the handle body 12.

In operation, as the movable handle 16 is initially moved from the open configuration, illustrated in FIG. 5, towards the closed configuration, the closure mechanism is disengaged from the first slider 22, allowing the jaw assembly to remain in an open configuration. But, the feed mechanism is engaged with the second slider 24, and the longitudinal slider 50 longitudinally distally advances the second slider 24 of the actuation assembly to load a clip into the jaw assembly. The handle body 12 can comprise at least one guide 30 positioned to maintain the drive plate 26 in engagement with the protruding fin 52 of the longitudinal slider 50 during the initial movement of the longitudinal slider 50.

Figure 6:
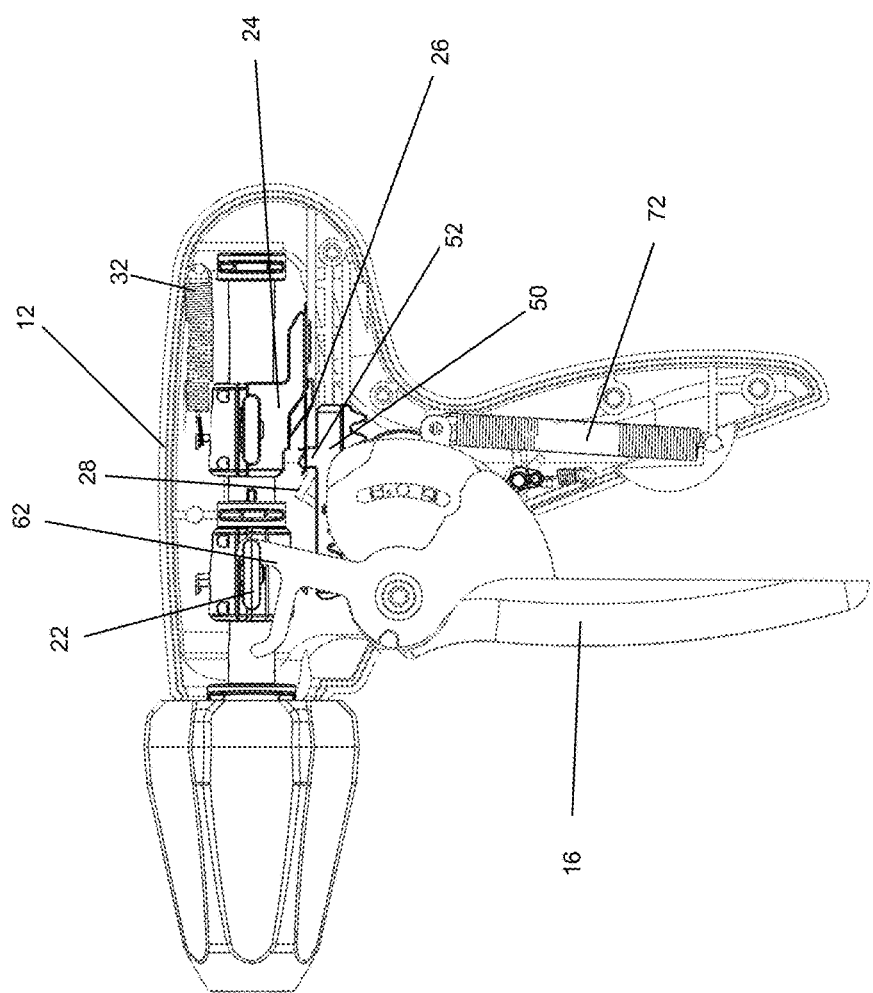
FIG. 6 is a cut-away side view of the handle assembly of FIG. 1 with a movable handle moved a first distance towards an approximated configuration.

With reference to FIG. 6, once the movable handle 16 has been moved a first distance from the open configuration, the closure fork 62 of the closure lever 60 engages the first slider 22 of the actuation assembly such that movement of the movable handle 16 beyond the first distance will longitudinally advance the first slider 22 to close the jaw assembly. Accordingly, movement of the movable handle 16 the first distance operates the feed mechanism to load a surgical clip that can then be clamped once the movable handle 16 is moved beyond the first distance. Thus, the feed mechanism of the handle assembly can be configured to disengage from the second slider 24 of the actuation assembly once the clip has been fed.

With reference to FIG. 6, the handle assembly can include a ramp 28 positioned and configured to disengage the drive plate 26 from the protrusion 52 or fin of the longitudinal slider 50. As the drive plate 26 is longitudinally advanced to engage the ramp 28 of the handle assembly, the distal end of the drive plate 26 is lifted to flex the drive plate 26. Once the drive plate 26 has been sufficiently flexed by the ramp, the drive plate 26 is lifted out of engagement with the fin of the longitudinal slider 50. With the second slider 24 of the actuation assembly disengaged from the longitudinal slider 50, a biasing member such as the tension spring 32, can rapidly withdraw the second slider 24 proximally. The feed mechanism of the handle assembly can be configured to completely load a clip and withdraw a feed member from the jaw assembly before the feed member can interfere with closure of the jaws. Thus, advantageously, the feed mechanism of the handle assembly can be configured to reduce the potential for clip feed jams.

Figure 7:
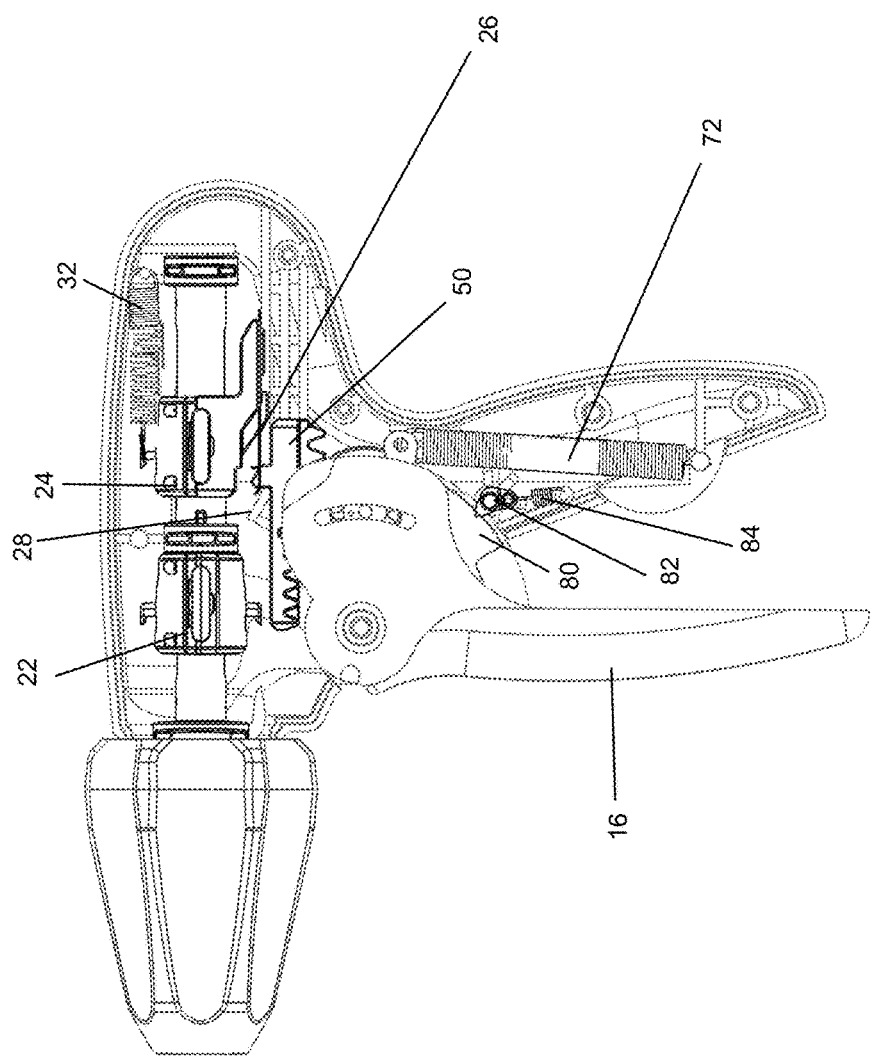
FIG. 7 is a cut-away side view of the handle assembly of FIG. 1 with the movable handle moved the first distance and illustrating a ratchet mechanism.

With reference to FIG. 7, a partial cut away view of the handle assembly is illustrated with the first clamp lever removed to further illustrate certain aspects of the handle assembly. In some embodiments, the handle assembly further comprises a ratchet mechanism to coordinate operation of the handle assembly to reduce the potential for clip feed jams. The ratchet mechanism can facilitate actuation of the movable handle through a complete actuation stroke corresponding to a complete clip feed and closure cycle of the feed and closure mechanisms before the movable handle can be returned to the open configuration for feed and closure of a subsequent clip.

With continued reference to FIG. 7, the illustrated ratchet mechanism comprises a ratchet rack 80 positioned on a ratchet plate that is coupled to the movable handle 16. The ratchet mechanism further comprises a ratchet pawl 82 coupled to the handle assembly. The ratchet mechanism can further include a pawl spring 84 coupling the ratchet pawl to the handle assembly to bias the ratchet pawl 82 into engagement with the ratchet rack 80 to provide a one-way ratchet mechanism. Once the movable handle 16 has been moved a predetermined distance from the open configuration towards the closed configuration, the ratchet pawl 82 engages a first tooth of the ratchet rack 80 such that the movable handle 16 can continue to move towards the closed configuration but is prevented from moving towards the open configuration by the ratchet mechanism.

Figure 8:
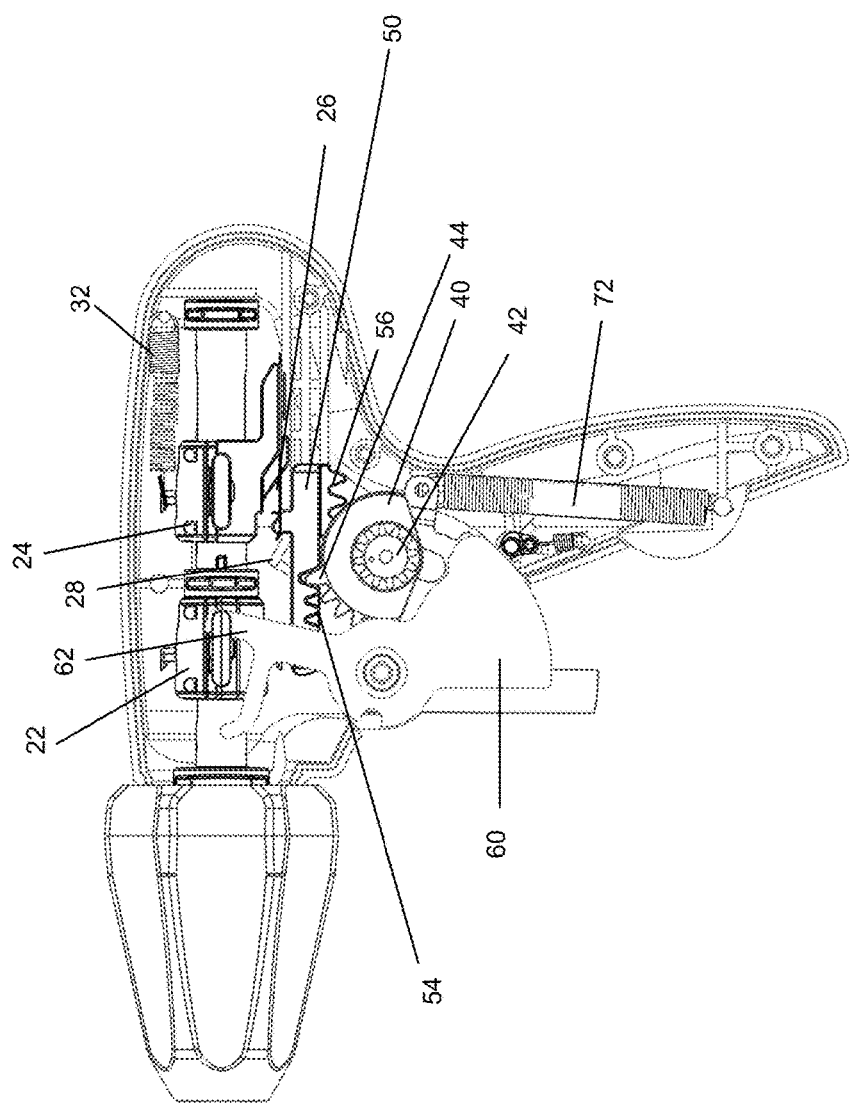
FIG. 8 is a cut-away side view of the handle assembly of FIG. 1 with the movable handle moved the first distance and illustrating a geared actuation mechanism.

With reference to FIG. 8, a partial cut away view of the handle assembly is illustrated with the grip member removed to further illustrate certain aspects of the handle assembly. As illustrated, the idler gear 40 comprises a pinion gear portion 42 positioned to engage a drive rack formed in a slot in the grip member. The idler gear 40 further comprises a first plurality of drive teeth 44 formed on an outer edge thereof that engage a first drive rack 54 on the longitudinal slider 50. In the illustrated embodiment, the feed mechanism comprises a gear train having sequentially-engageable gearing to define corresponding sequential longitudinal slider advancement profiles. For example, in the illustrated embodiment, the idler gear 40 comprises a first plurality of drive teeth 44 formed on an outer edge thereof that define a first advancement profile of the longitudinal slider defined by the longitudinal slider advancing a first longitudinal distance per degree of rotation of the movable handle and a second plurality of drive teeth that define a second advancement profile of the longitudinal slider.

With continued reference to FIG. 8, once the longitudinal slider 50 has been advanced the first distance, a second plurality of drive teeth 46 (FIG. 12) engage a second drive rack 56 on the longitudinal slider 50 to define a second advancement profile of the longitudinal slider 50. In certain embodiments, the second plurality of drive teeth 46 can be formed on a surface of the idler gear opposite the pinion gear. In certain embodiments, the second plurality of drive teeth 46 can be positioned radially inwardly of the first plurality of drive teeth 44 with respect to the rotational axis of the idler gear 40. The second drive rack 56 can likewise be positioned to engage the radially-inwardly positioned drive teeth. With radial inward positioning, movement of the movable handle a given distance results in a second advancement profile defined by a relatively smaller longitudinal translation of the longitudinal slider per rotation of the movable handle 16 when the second drive rack 56 is engaged with the second plurality of drive teeth 46 as compared to when the first drive rack 54 is engaged with the first plurality of drive teeth 44. Advantageously, the sequentially-engageable gearing of the illustrated embodiment can reduce the total longitudinal translation of the longitudinal slider as the movable handle is actuated from the open configuration to the closed configuration. Thus, desirably, the handle body can have a relatively compact length enhancing usability and reducing packaging and storage requirements.

In some embodiments, the sequentially-engageable gearing of the gear train can comprise a transition region to facilitate a smooth transition from engagement of the first plurality of drive teeth 44 with the first drive rack 54 to engagement of the second plurality of drive teeth 46 with the second drive rack 56. For example, in the illustrated embodiment, the first plurality of drive teeth 44 comprises a plurality of teeth having a first size and at least one transition tooth having a second size larger than the first size. The first drive rack 54 comprises a corresponding plurality of teeth arranged to receive the plurality of teeth having the first size and at least one tooth arranged to receive the at least one transition tooth of the first plurality of drive teeth. The relatively large size of the at least one transition tooth maintains geared engagement between the longitudinal slider 50 and the idler gear 40 throughout a transition from the first plurality of drive teeth 44 and first drive rack 54 and the second plurality of drive teeth 46 and the second drive rack 56.

Figure 9:
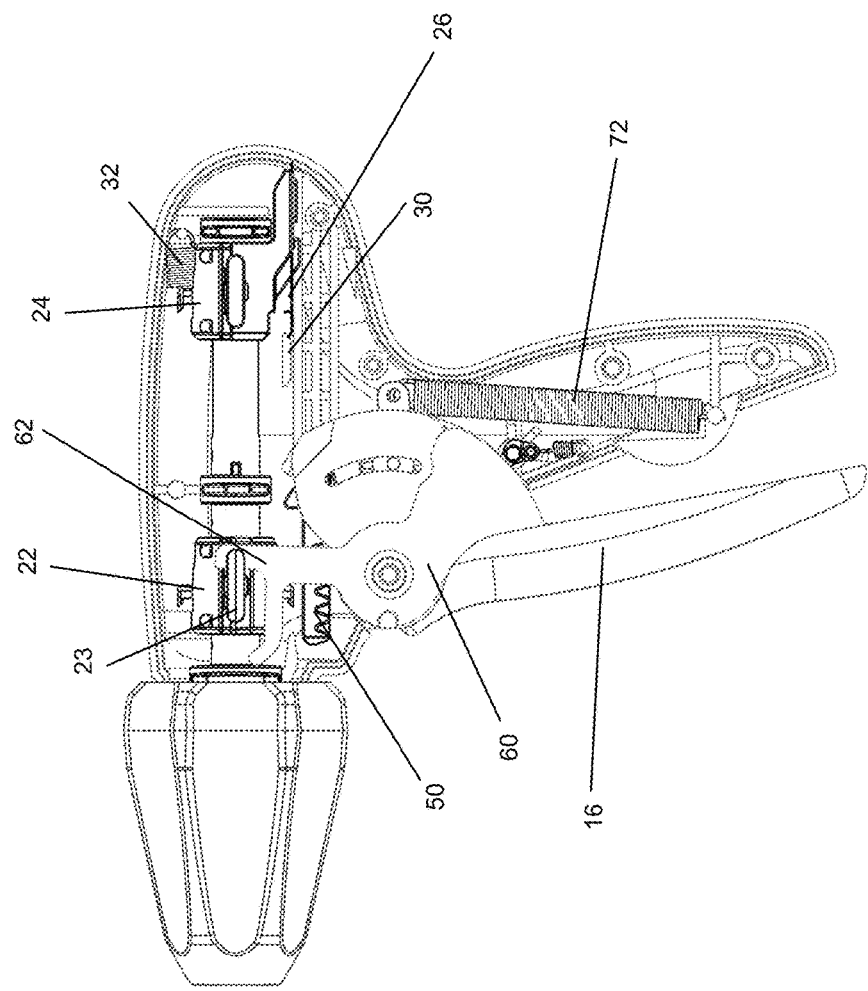
FIG. 9 is a cut-away side view of the handle assembly of FIG. 1 with a movable handle moved a second distance towards an approximated configuration.

With reference to FIG. 9, an embodiment of handle assembly is illustrated with the movable handle 16 approaching a closed configuration. As illustrated, the second slider 24 of the actuation mechanism has been disengaged from the feed mechanism and proximally withdrawn by the tension spring 32. In certain embodiments with a sequentially-engageable gearing, the second plurality of drive teeth of the idler gear has engaged the second rack of the longitudinal slider 50 of the feed mechanism. Accordingly, continued movement of the movable handle 16 past the first distance to feed a clip moves the longitudinal slider 50 a relatively short distance relative to the handle body.

With continued reference to FIG. 9, the movable handle 16 of the illustrated handle assembly is approaching the closed configuration having moved a second distance beyond the first distance. Over the second distance, the closure fork 62 of the closure lever 60 has advanced the first slider 22 of the actuation assembly to clamp a clip positioned in the jaw assembly. Advantageously, in the illustrated embodiment the first slider 22 is directly connected to the movable handle 16 at the lug 23 of the first slider 22, providing tactile feedback to the user as the clip is clamped.

Figure 10:
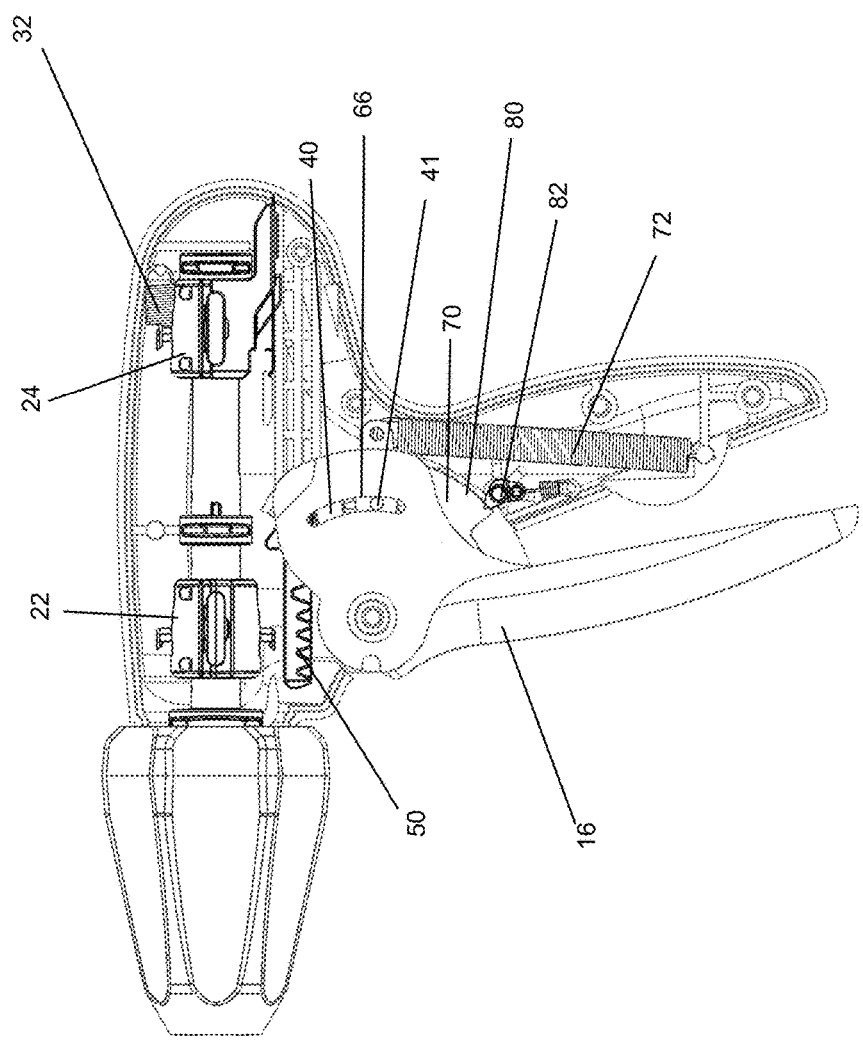
FIG. 10 is a cut-away side view of the handle assembly of FIG. 1 with the movable handle moved the second distance and illustrating a ratchet mechanism.

With reference to FIG. 10, a partial cut-away view of the handle assembly is illustrated with the first closure lever hidden to illustrate certain aspects of the handle assembly. As illustrated, with the movable handle 16 approaching the closed configuration, the ratchet pawl 82 of the ratchet mechanism can be approaching a last tooth of the ratchet rack 80 positioned on a ratchet plate 70 of the movable handle 16. Once the ratchet pawl 82 has been advanced past the last tooth of the ratchet rack 80, the movable handle 16 can be returned to the open configuration without restriction from the ratchet mechanism. In various embodiments, the ratchet mechanism can be configured such that ratchet pawl 82 passes the last tooth of the ratchet rack 80 only after the clip has been substantially fully closed. In other embodiments, the ratchet mechanism can be configured such that the ratchet pawl 82 passes the last tooth of the ratchet rack 80 once the clip has been partially closed.

With continued reference to FIG. 10, the movable handle 16 can comprise an arcuate slot 66 formed therethrough to accommodate a rotational hub 41 of the idler gear 40. Accordingly, the idler gear 40 can be rotatably coupled to both handle halves of the handle body such as by a pinned connection extending through the movable handle 16. In some embodiments, the arcuate slot 66 can have ends defining an actuation stroke from an open configuration of the movable handle 16 to a closed configuration of the movable handle 16. In other embodiments, the arcuate slot 66 can have a length that is longer than the actuation stroke of the movable handle 16, such that the slot 66 has ends that are spaced apart from the rotational hub 41 of the idler gear 40 when the movable handle 16 is in the open configuration or the closed configuration.

Figure 11:
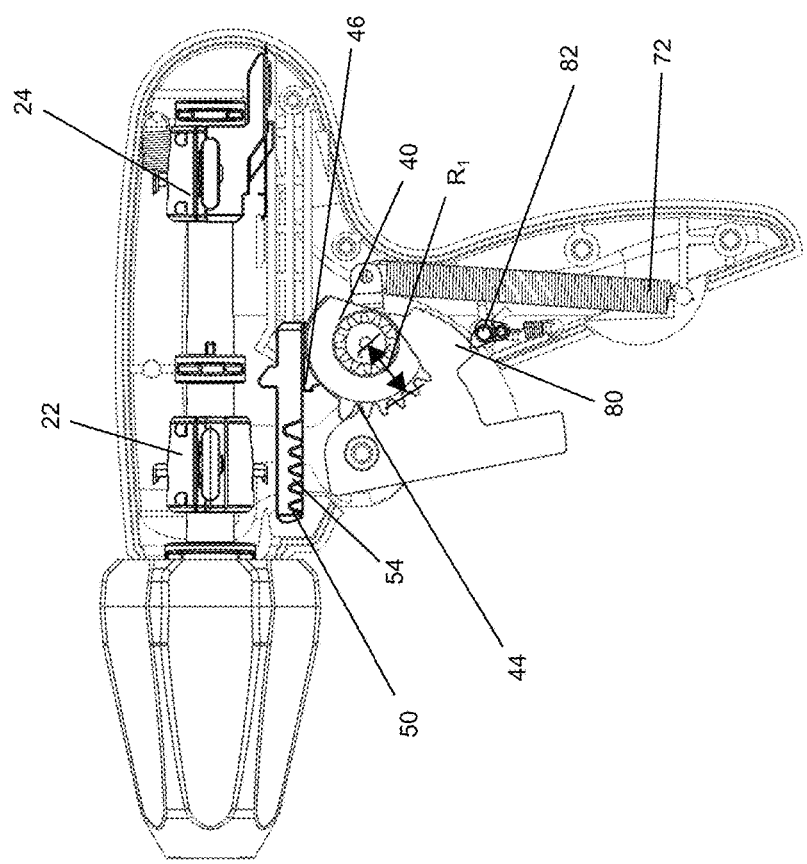
FIG. 11 is a cut-away side view of the handle assembly of FIG. 1 with the movable handle moved the second distance and illustrating a geared actuation mechanism.
Figure 12:
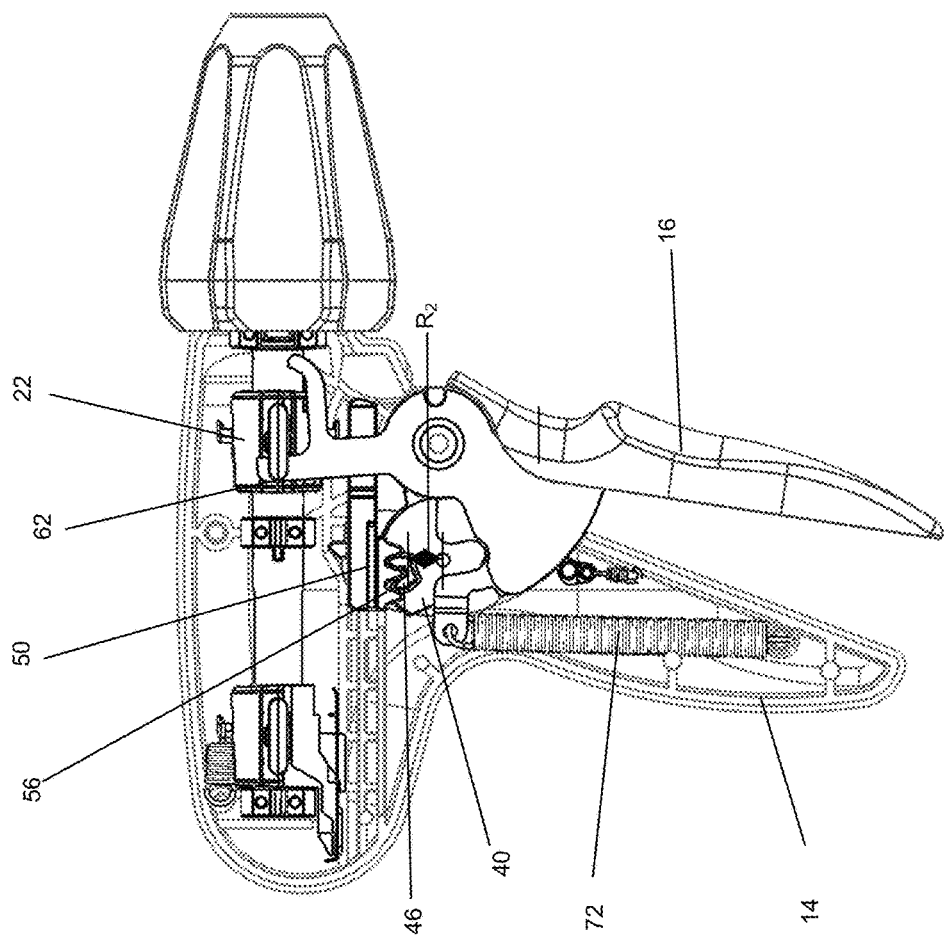
FIG. 12 is a cut-away side view of the handle assembly of FIG. 11 from an opposite side of the handle assembly.

With reference to FIG. 11, a partial cut-away view of the handle assembly is illustrated with the first closure lever and grip member hidden to illustrate certain aspects of the handle assembly. As illustrated, the second plurality of gear teeth 46 of the idler gear 40 is engaged with the second rack on the longitudinal slider 50. Moreover the first plurality of gear teeth 44 of the idler gear 40 is disengaged from the first rack 54 on the longitudinal slider 50. FIG. 12 illustrates a partial cut-away view of the handle assembly from an opposite side of the handle assembly. As illustrated, the second plurality of gear teeth 46 is disposed on a face of the idler gear 40 opposite the pinion gear portion. Moreover, the second plurality of gear teeth 46 is positioned at a second radial distance $R_2$ from the rotational axis of the idler gear 40. The second rack 56 is positioned on the longitudinal slider 50 to engage the second plurality of drive teeth 46. In the illustrated embodiment, the second radial distance $R_2$ is relatively small compared to a first radial distance $R_1$ of the first plurality of drive teeth 44 (FIG. 11).

Figure 13:
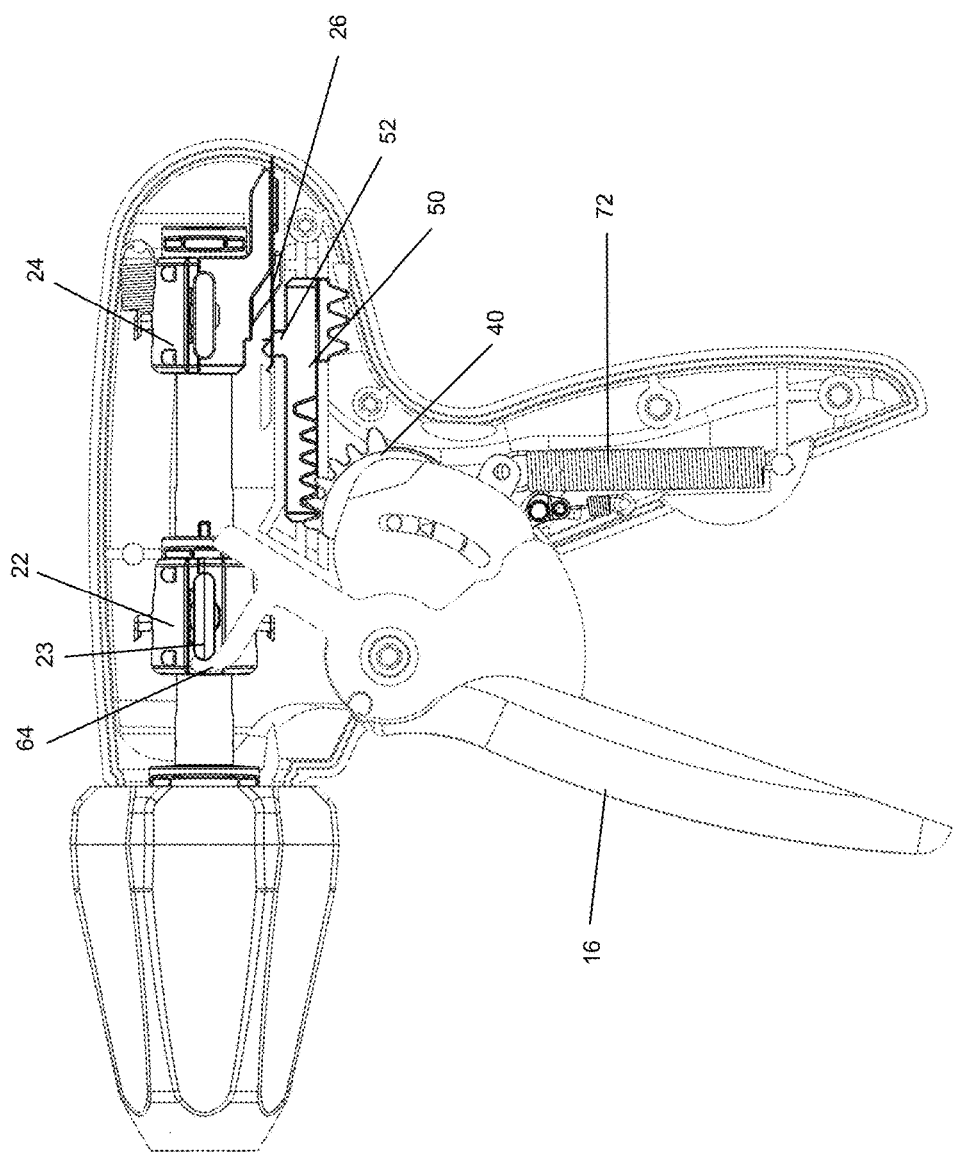
FIG. 13 is a cut-away side view of the handle assembly of FIG. 1 with the movable handle returned to the spaced apart configuration.

With reference to FIG. 13, an embodiment of handle assembly is illustrated with the movable handle returned to the open configuration. Once a clip feed and closure cycle has been completed, as illustrated in FIGS. 5-12, the movable handle 16 can be released to return the movable handle 16 to the open configuration. A biasing member such as a handle spring 72 can bias the movable handle 16 into the open configuration. As the movable handle 16 is moving towards the open configuration, the retraction fork 64 of the closure lever can proximally retract the first slider 22 of the actuation assembly. This retraction of the first slider 22 opens the jaws of the jaw assembly. Additionally, while the movable handle 16 is moving towards the open configuration, it rotates the idler gear 40, which returns the longitudinal slider 50 proximally to the proximal position. As the longitudinal slider 50 nears the proximal position, the protrusion 52 fin of the longitudinal slider 50 engages the drive plate 26. The fin on the longitudinal slider 50 can include a tapered or ramped profile at the proximal end thereof to guide the drive plate 26 into a flexed configuration and into engagement with the fin. Thus, once the handle assembly has been returned to the open configuration, the feed mechanism is engaged with the second slider 24 to feed a subsequent clip when the movable handle is subsequently closed.

Figure 14:
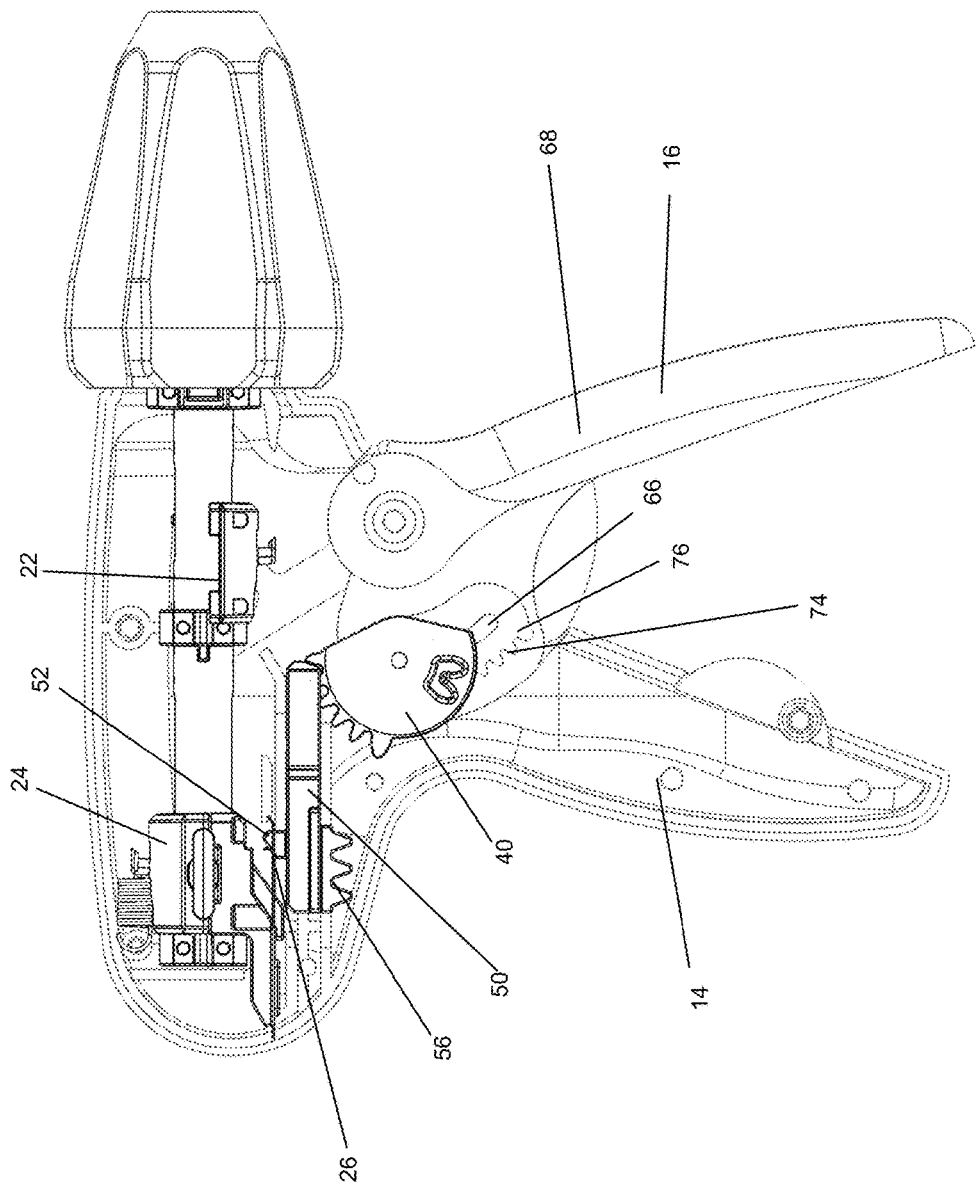
FIG. 14 is a cut-away side view of the handle assembly of FIG. 13 from an opposite side of the handle assembly illustrating a geared actuation mechanism.

With reference to FIG. 14, a partial cut away of an embodiment of handle assembly is illustrated with the second clamp lever hidden to visualize certain aspects of the handle assembly. As illustrated, the movable handle 16 comprises a drive rack 74 formed therein that engages the pinion gear portion of the idler gear 40. The drive rack 74 can be positioned in a recess 76 or slot formed in the grip member 68 of the movable handle 16. The recess can 76 have a generally arcuate profile such that the movable handle 16 can be pivotally moved relative to the handle body and the rotational axis of the idler gear 40. In the illustrated embodiment, the drive rack 74 is positioned in a recess 76 formed in the grip member 68 of the movable handle 16. As illustrated, the grip member 68 also includes an arcuate slot 66 formed through the recess 76 to accommodate a rotational coupling, such as a pivot pin, of the idler gear 40 to the handle assembly.

With reference to FIGS. 15A-D, an embodiment of idler gear 40 for the handle assemblies discussed herein is illustrated. The illustrated idler gear 40 is configured to provide sequentially-engageable gearing. Accordingly, the idler gear 40 includes a pinion gear portion 42 positioned on a first surface 43 thereof, a first plurality of gear teeth 44 positioned on an edge 45 thereof, and a second plurality of teeth 46 positioned on a second surface 47 thereof opposite the first surface 43. The idler gear 40 further comprises a rotational hub 41 extending through the pinion gear portion 42.

Figure 15A:
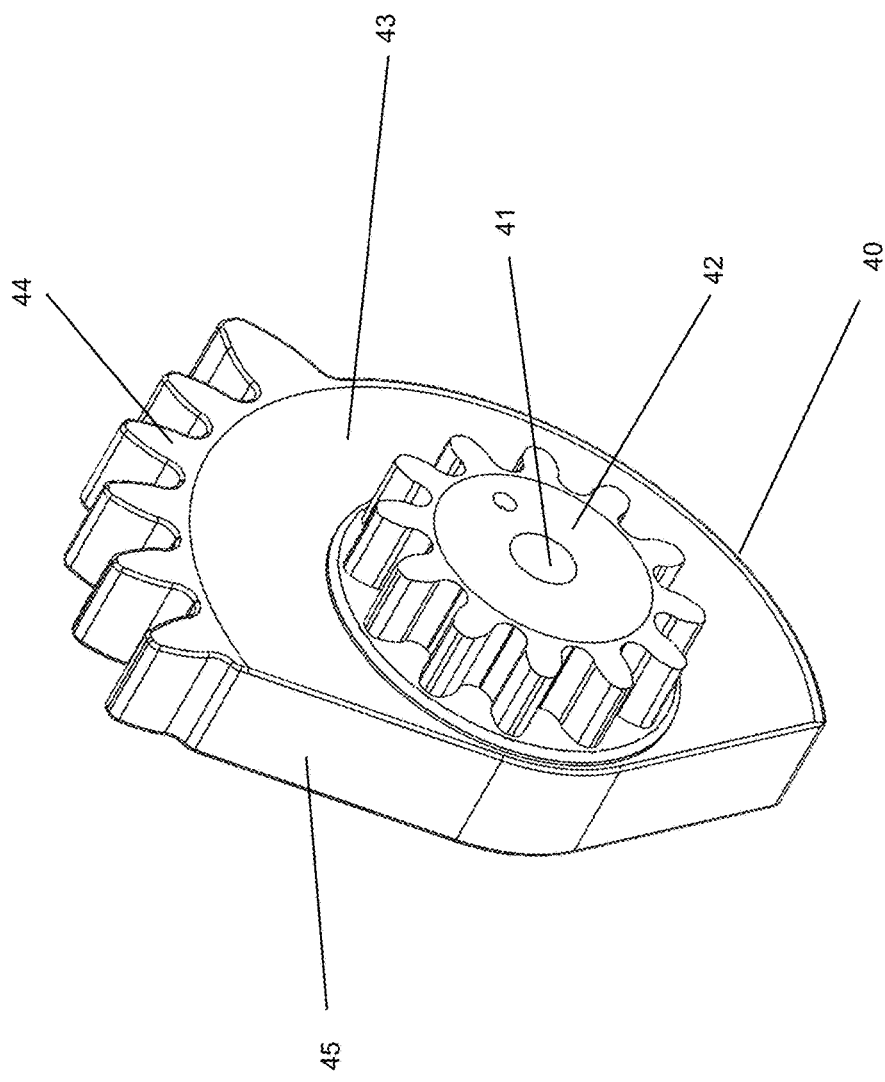
FIG. 15A is a perspective view of an idler gear of the geared actuation mechanism of FIG. 14.
Figure 15B:
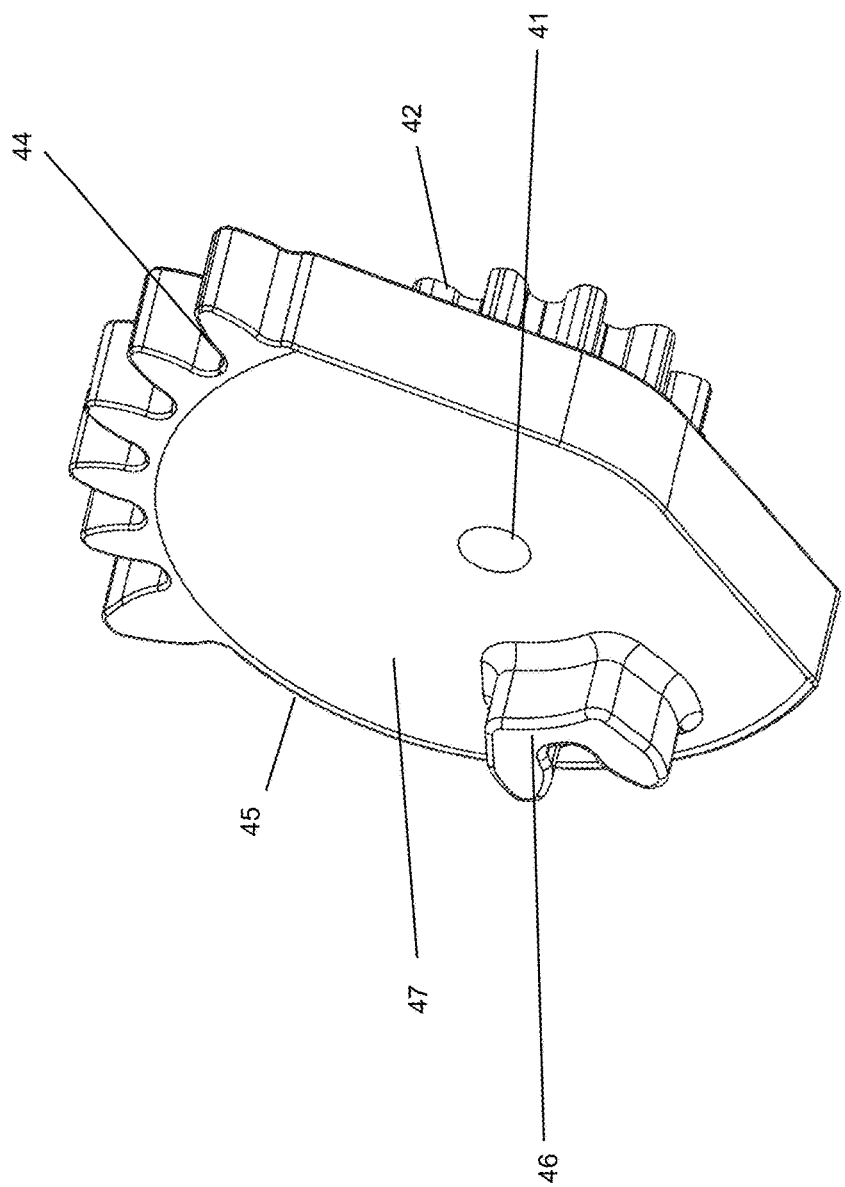
FIG. 15B is a perspective view of the idler gear of FIG. 15A.
Figure 15C:
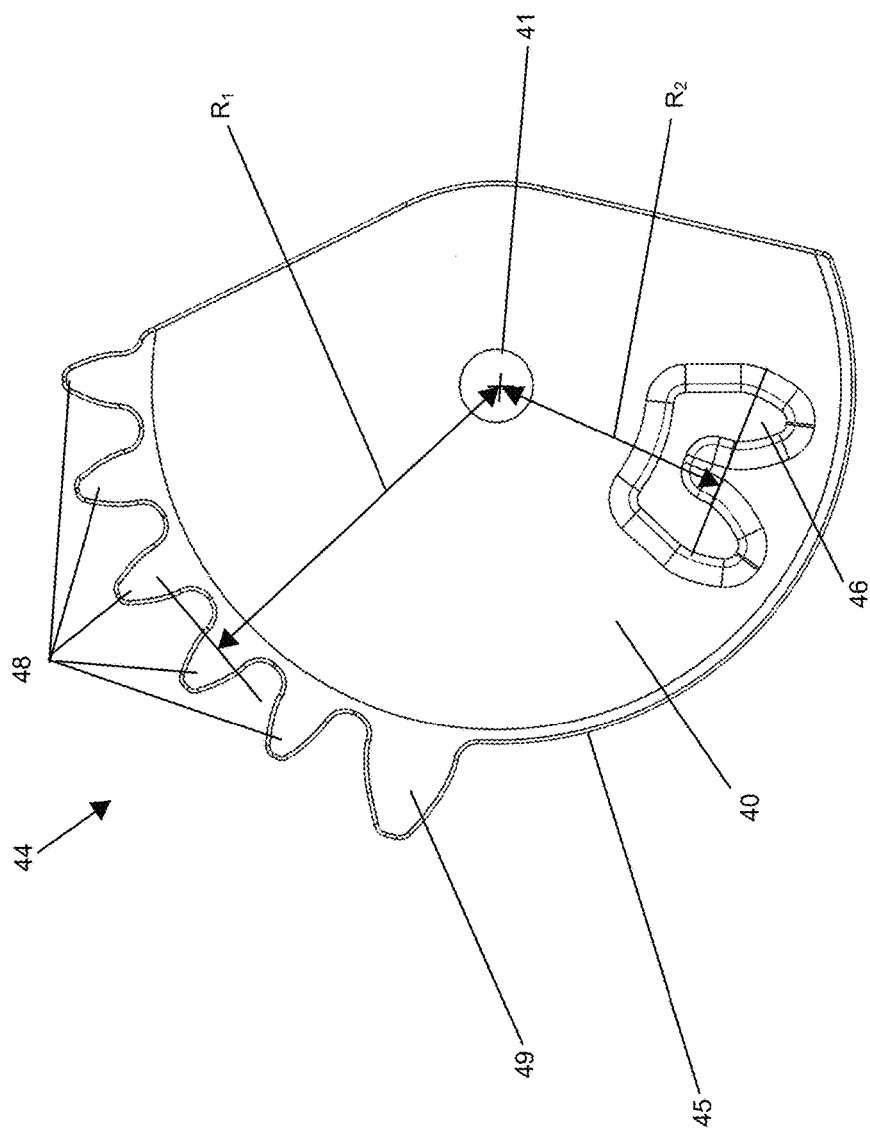
FIG. 15C is a side view of the idler gear of FIG. 15A.
Figure 15D:
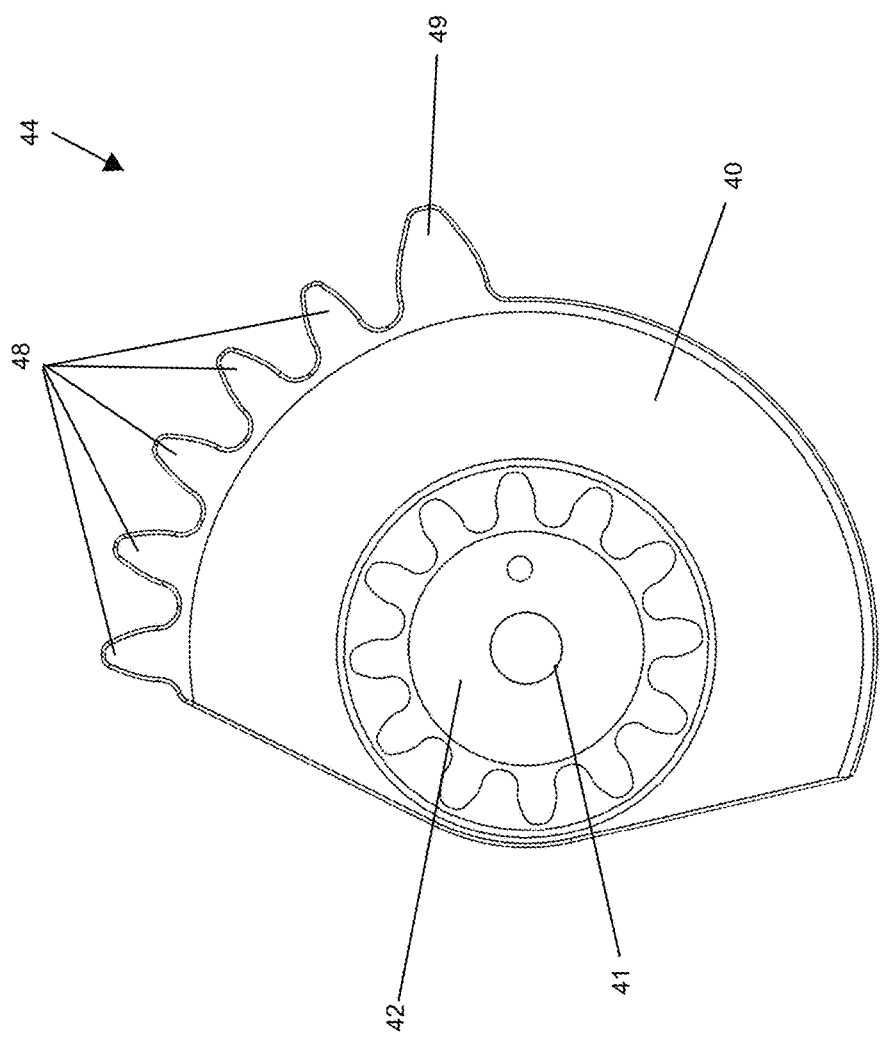
FIG. 15D is a side view of the idler gear of FIG. 15C from an opposite side.

With continued reference to FIGS. 15A-D, the sequentially-engageable gearing profile of the illustrated idler gear 40 includes one plurality of gear teeth at a rotational radius that is relatively large compared to the rotational radius of the other plurality of gear teeth, allowing the longitudinal slider to be driven along an advancement profile that can vary relative to an input rotation of the pinion gear portion. For example, the first plurality of gear teeth 44 can be positioned at a first radial distance $R_1$ from the rotational hub 41, and the second plurality of gear teeth can be positioned at a second radial distance $R_2$ from the rotational hub 41, smaller than the first radial distance $R_1$. (FIG. 15C). In other embodiments of handle assembly, other arrangements of idler gear can be used. For example, the positions of the pinion, first, and second plurality of drive teeth on the surfaces and edge of the idler gear can be varied from the illustrated embodiment.

In the illustrated embodiment, the sequentially-engageable gearing of the idler gear 40 comprises a transition region to facilitate a smooth transition from engagement of the first plurality of drive teeth 44 with the first drive rack to engagement of the second plurality of drive teeth 46 with the second drive rack. In some embodiments, one of the plurality of drive teeth 44, 46 can include an asymmetric profile to define the transition region. As illustrated, the first plurality of drive teeth 44 comprises a plurality of teeth 48 having a first size and at least one transition tooth 49 having a second size larger than the first size. The first drive rack comprises a corresponding plurality of teeth arranged to receive the plurality of teeth having the first size and at least one tooth arranged to receive the at least one transition tooth 49 of the first plurality of drive teeth 44. The second plurality of drive teeth 46 in the illustrated embodiment includes a plurality of teeth having a generally symmetric configuration such that each tooth has a substantially identical geometric profile. In some embodiments, it is contemplated that the second plurality of drive teeth 46 can also have an asymmetric profile including a transition tooth having a different size instead of or in addition to the transition tooth 49 on the first plurality of drive teeth 44.

In certain embodiments, the handle assemblies described herein can be configured to provide a desired operating sequence. For example, in some embodiments, the movable handle can be pivotable over an approximately 40 degree actuation stroke from an open configuration to a closed configuration. The feed mechanism is actuated over approximately the first 18 degrees of the actuation stroke to load a clip into the jaw assembly. The closure mechanism is actuated over the remaining 22 degrees of the actuation stroke. Advantageously, the geared clip feed mechanism allows a clip to be loaded with a relatively constant force profile compared to a lever-actuated loading mechanism, enhancing user operability. Moreover, the direct connection of the movable handle to the front slider via the lever enhances user feel during the clip clamping portion of the actuation stroke. In other embodiments, the actuation stroke, feed mechanism portion, and closure mechanism portion can have other arc lengths as may be desired to configure the handle to have a desired clip load force, user feedback, or to house the feed and closure mechanisms in a desired handle assembly size and shape.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims.

What is claimed is:

1. A laparoscopic surgical clip applier comprising:
    a jaw assembly comprising a pair of opposed jaws configured to receive and clamp a surgical clip;
    a shaft assembly extending from a proximal end to a distal end, the jaw assembly positioned at the distal end of the shaft assembly, and the shaft assembly comprising a clamping slider and a feed slider disposed at the proximal end thereof; and
    a handle assembly disposed at the proximal end of the shaft assembly, the handle assembly comprising:
        a stationary handle;
        a movable handle pivotably coupled to the stationary handle;
        a clamping actuator coupled to the movable handle, the clamping actuator comprising:
            a clamping fork extending from the clamping actuator and configured to distally advance the clamping slider; and
            a return fork extending from the clamping actuator and configured to proximally retract the clamping slider; and
        a feed mechanism comprising:
            an idler gear rotatably driven by the movable handle, the idler gear comprising a first plurality of drive teeth and a second plurality of drive teeth; and
            a slider longitudinally movable within the handle assembly, the slider comprising a first gear rack engageable with the first plurality of drive teeth and a second gear rack engageable with the second plurality of drive teeth, wherein the slider is engageable with the feed slider.

2. The laparoscopic surgical clip applier of claim 1, wherein the clamping fork is spaced apart from the return fork.

3. The laparoscopic surgical clip applier of claim 1, wherein the clamping actuator extends from the movable handle.

4. The laparoscopic surgical clip applier of claim 1, wherein the idler gear is coupled to the stationary handle at a rotational axis and wherein the movable handle comprises a slot formed therein to receive the idler gear at the rotational axis.

5. The laparoscopic surgical clip applier of claim 4, wherein the slot of the movable handle comprises a feed mechanism rack formed therein.

6. The laparoscopic surgical clip applier of claim 5, wherein the idler gear comprises a drive pinion gear engaged with the feed mechanism rack of the movable handle.

7. The laparoscopic surgical clip applier of claim 1, wherein the idler gear comprises a plate having a first surface, a second surface opposite the first surface and an edge extending between the first surface and the second surface and wherein the first plurality of drive teeth is positioned on one of the first surface, the second surface, and the edge and the second plurality of drive teeth is positioned on another of the first surface, the second surface, and the edge.

8. The laparoscopic surgical clip applier of claim 7, wherein the idler gear further comprises a drive pinion gear positioned one of the first surface, the second surface, and the edge not having the first plurality of drive teeth and the second plurality of drive teeth.

9. The laparoscopic surgical clip applier of claim 1, wherein the feed slider is coupled to a flexible drive plate and wherein the slider comprises a tab engageable with the flexible drive plate.

10. The laparoscopic surgical clip applier of claim 9, wherein the handle assembly further comprises a ramp positioned to deflect the flexible drive plate out of engagement with the tab of the slider once the slider has been longitudinally advanced a predetermined distance.

11. The laparoscopic surgical clip applier of claim 10, wherein the feed mechanism further comprises a return spring biasing the feed slider into a retracted position when the flexible drive plate has been disengaged from the tab of the slider.

12. The laparoscopic surgical clip applier of claim 10, wherein the clamping fork engages the clamping slider once the slider has been longitudinally advanced the predetermined distance.

13. A laparoscopic clip applier comprising:
a jaw assembly comprising a pair of opposed jaws configured to receive and clamp a surgical clip;
a shaft assembly extending from a proximal end to a distal end, the jaw assembly positioned at the distal end of the shaft assembly, and the shaft assembly comprising a plurality of surgical clips disposed within the shaft assembly; and
a handle assembly disposed at the proximal end of the shaft assembly, the handle assembly comprising:
a stationary handle;
a movable handle pivotably coupled to the stationary handle;
a feed mechanism comprising a gear train coupled to the movable handle and coupled to the shaft assembly to feed a distal surgical clip of the plurality of surgical clips into the jaw assembly; and
a clamping mechanism coupled to the jaw assembly to clamp the pair of opposed jaws of the jaw assembly;
wherein the movable handle is movable from a spaced apart configuration relative to the stationary handle to an approximated configuration relative to the stationary handle, the movable handle movable over a first distance from the spaced apart configuration to actuate the feed mechanism and movable over a second distance from the first distance to the approximated configuration to actuate the clamping mechanism.

14. The laparoscopic clip applier of claim 13, wherein the first distance comprises a pivotal movable handle sweep defining an angular arc of greater than 15 degrees.

15. The laparoscopic clip applier of claim 13, wherein the second distance comprises a pivotal movable handle sweep defining an angular arc of greater than 20 degrees.

16. The laparoscopic clip applier of claim 13, wherein the clamping mechanism comprises a clamping fork having a clamping arm spaced apart from a return arm.

17. The laparoscopic clip applier of claim 13, wherein the gear train of the feed mechanism comprises:
an idler gear driven by pivotal movement of the movable handle, the idler gear comprising a plurality of drive gear teeth; and
a slider longitudinally slidable within the handle assembly, the slider comprising a gear rack engageable with the drive gear teeth to longitudinally slide the slider, and the slider engageable with the proximal end of the shaft assembly.

18. The laparoscopic clip applier of claim 17, wherein the idler gear further comprises a second plurality of drive teeth and wherein the slider further comprises a second gear rack engageable with the second plurality of drive teeth.

19. The laparoscopic clip applier of claim 13, wherein the handle assembly further comprises a ratchet mechanism coupled to the movable handle such that once the ratchet mechanism is engaged, movement of the movable handle towards the spaced apart configuration is prevented and movement of the movable handle completely to the approximated configuration disengages the ratchet mechanism.

20. A laparoscopic clip applier comprising:
a jaw assembly comprising a pair of opposed jaws configured to receive and clamp a surgical clip;
a shaft assembly extending from a proximal end to a distal end, the jaw assembly positioned at the distal end of the shaft assembly, and the shaft assembly comprising a first slider and a second slider at the proximal end; and
a handle assembly comprising:
a stationary handle;
a movable handle pivotably coupled to the stationary handle;
a first actuation mechanism coupled to the movable handle and to the first slider; and
a second actuation mechanism, the second actuation mechanism comprising:
a drive gear rotatably driven by pivotal movement of the movable handle, the drive gear having a first plurality of teeth and a second plurality of teeth; and
a longitudinal slider having a first rack engageable with the first plurality of teeth and a second rack engageable with the second plurality of teeth, the longitudinal slider engageable with the second slider of the shaft assembly.

21. The laparoscopic clip applier of claim 20, wherein the first actuation mechanism comprises a forked actuator having a first fork to longitudinally advance the first slider and a second fork to longitudinally retract the first slider.

22. The laparoscopic clip applier of claim 20, wherein the first plurality of teeth have a first pitch diameter and the second plurality of teeth have a second pitch diameter different from the first pitch diameter.

23. The laparoscopic clip applier of claim 20, wherein the first plurality of teeth comprise at least one tooth having a transition profile.

* * * * *